(12) United States Patent
Jerke et al.

(10) Patent No.: US 9,750,512 B2
(45) Date of Patent: Sep. 5, 2017

(54) DRILL GUIDE FOR INSTALLING A BONE PLATE

(71) Applicant: Zimmer Spine, Inc., Minneapolis, MN (US)

(72) Inventors: Eric P. Jerke, Bloomington, MN (US); Peter G. Schulte, Richmond, MN (US); David W. Castleman, Minneapolis, MN (US); Andrew Olson, Champlin, MN (US); Jack A. Dant, St. Paul, MN (US); Eric J. Lundequam, Hopkins, MN (US); Hugh D. Hestad, Edina, MN (US)

(73) Assignee: Zimmer Spine, Inc., Edina, MN (US)

( * ) Notice: Subject to any disclaimer, the term of this patent is extended or adjusted under 35 U.S.C. 154(b) by 990 days.

(21) Appl. No.: 14/058,601

(22) Filed: Oct. 21, 2013

(65) Prior Publication Data
US 2015/0112353 A1    Apr. 23, 2015

(51) Int. Cl.
    *A61B 17/17*    (2006.01)
(52) U.S. Cl.
    CPC ................................. *A61B 17/1728* (2013.01)
(58) Field of Classification Search
    CPC .. A61B 17/17; A61B 17/1728; A61B 17/1757
    See application file for complete search history.

(56) References Cited

U.S. PATENT DOCUMENTS

| | | |
|---|---|---|
| 4,465,065 A | 8/1984 | Gotfried et al. |
| 5,180,388 A | 1/1993 | Dicarlo |
| 5,306,278 A | 4/1994 | Dahl et al. |
| 5,364,399 A | 11/1994 | Lowery et al. |
| 5,423,826 A | 6/1995 | Coates et al. |
| 5,531,751 A | 7/1996 | Schultheiss et al. |
| 5,669,915 A | 9/1997 | Caspar et al. |
| 5,676,666 A | 10/1997 | Oxland et al. |
| 5,741,266 A | 4/1998 | Moran et al. |
| 5,755,721 A | 5/1998 | Hearn |
| 5,769,856 A | 6/1998 | Dong et al. |
| 5,851,207 A | 12/1998 | Cesarone |
| 5,899,908 A | 5/1999 | Kuslich et al. |
| 6,059,789 A | 5/2000 | Dinger et al. |
| 6,066,142 A | 5/2000 | Serbousek et al. |
| 6,193,720 B1 | 2/2001 | Yuan et al. |
| 6,193,721 B1 | 2/2001 | Michelson |
| 6,235,034 B1 | 5/2001 | Bray |
| D449,692 S | 10/2001 | Michelson |
| 6,342,056 B1 | 1/2002 | Mac-Thiong et al. |
| 6,342,057 B1 | 1/2002 | Brace et al. |
| 6,379,364 B1 | 4/2002 | Brace et al. |

(Continued)

*Primary Examiner* — Anu Ramana
(74) *Attorney, Agent, or Firm* — Schwegman Lundberg & Woessner, P.A.

(57) ABSTRACT

An adjustable apparatus for guiding medical instruments used in attaching bone plates. The apparatus has a handle assembly, guide member, a spacer, and an actuation member. The actuation member extends from the handle assembly and actuates the spacer between a position adjacent the guide member and a position spaced from the guide member. The spacer has a through hole that may axially align with a lumen extending through the guide member when in the first position and which is moved out of axial alignment with the lumen in the second position. The spacer may function as a depth stop to control the maximum depth a drill bit can extend from the guide member.

17 Claims, 11 Drawing Sheets

(56) References Cited

U.S. PATENT DOCUMENTS

| | | |
|---|---|---|
| 6,398,783 B1 | 6/2002 | Michelson |
| 6,416,528 B1 | 7/2002 | Michelson |
| 6,454,771 B1 | 9/2002 | Michelson |
| 6,592,586 B1 | 7/2003 | Michelson |
| 6,692,503 B2 | 2/2004 | Foley et al. |
| 7,011,665 B2 | 3/2006 | Null et al. |
| 7,081,119 B2 | 7/2006 | Stihl |
| 7,094,242 B2 | 8/2006 | Ralph et al. |
| 7,131,974 B2 | 11/2006 | Keyer et al. |
| 7,163,542 B2 | 1/2007 | Ryan |
| 7,166,111 B2 | 1/2007 | Kolb et al. |
| 7,357,804 B2 | 4/2008 | Binder, Jr. et al. |
| 7,422,594 B2 | 9/2008 | Zander et al. |
| 7,442,197 B2 | 10/2008 | Abdelgany |
| 7,621,942 B2 | 11/2009 | Piehl |
| 8,007,449 B2 | 8/2011 | Kotmel et al. |
| 8,109,934 B2 | 2/2012 | Guenther et al. |
| 8,147,527 B2 | 4/2012 | Hoffman et al. |
| 8,246,662 B2 | 8/2012 | Lemoine et al. |
| 8,337,496 B2 | 12/2012 | Piehl |
| 8,628,530 B2 | 1/2014 | Hajianpour |
| 2002/0045896 A1 | 4/2002 | Michelson |
| 2002/0147450 A1 | 10/2002 | LeHuec et al. |
| 2002/0156481 A1 | 10/2002 | Boyd et al. |
| 2003/0083667 A1 | 5/2003 | Ralph et al. |
| 2004/0015174 A1 | 1/2004 | Null |
| 2004/0092947 A1 | 5/2004 | Foley |
| 2004/0186482 A1 | 9/2004 | Kolb et al. |
| 2004/0267274 A1 | 12/2004 | Patel et al. |
| 2005/0015092 A1 | 1/2005 | Rathbun et al. |
| 2005/0015093 A1 | 1/2005 | Suh et al. |
| 2005/0038444 A1 | 2/2005 | Binder et al. |
| 2005/0228400 A1 | 10/2005 | Chao et al. |
| 2006/0155284 A1 | 7/2006 | Doherty et al. |
| 2007/0055286 A1 | 3/2007 | Ralph et al. |
| 2007/0233150 A1 | 10/2007 | Blain et al. |
| 2007/0288031 A1 | 12/2007 | Dreyfuss et al. |
| 2008/0009881 A1 | 1/2008 | Blatt et al. |
| 2008/0154280 A1 | 6/2008 | Schumacher et al. |

DRILL GUIDE FOR INSTALLING A BONE PLATE

TECHNICAL FIELD

The disclosure is directed to medical instrument guide devices. More particularly, the disclosure is directed to instrument guide devices for guiding a bone drill or other installation tools.

BACKGROUND

When attaching a bone plate to a bone of a patient, medical professionals need to perform drilling, tapping, and/or screwing steps. When performing these tasks, it is often beneficial for the hole, threads, or screw to be straight, for the drilling, tapping, and/or screwing tool to reduce excess lateral pressure to the bone that could weaken or break the bone around the hole, for the medical professional to know a depth of the drill bit within a patient, and for the medical professional to control the maximum depth of the drill bit within the patient. For example, when drilling, tapping, or screwing in order to attach a plate to underlying bone, the holes should be straight into the bone at an angle that promotes solid attachment and to a precise, controlled depth.

Early solutions for attaching a plate to underlying bone involved drilling, tapping, and/or screwing without any guide. Without a guide, the surgeon had to maintain a particularly steady hand and had to rely on judging the angle of entry and depth with the naked eye. Eventual solutions involved drilling and tapping a hole through a guide, then removing the guide and screwing the screw into the hole by hand or without the aid of a guide.

SUMMARY

The disclosure is directed to several alternative or complementary designs, materials, and methods of using medical device structures and assemblies. Although it is noted that conventional medical instrument guide devices exist, there exists a need for improvement on those devices.

Accordingly, one illustrative embodiment of the disclosure is an apparatus for guiding medical instruments used in attaching bone plates (e.g., occipital plates, cervical plates, and/or other bone plates) to patients. The apparatus may have a handle assembly, a guide member, a spacer, and an actuation member. Illustratively, the guide member may extend from the handle assembly and may include a first end, a second end, and a lumen extending therethrough from the first end to the second end. The spacer may be adjustably positionable at the first end of the guide member in response to actuation and/or adjustment of the actuation member. The spacer may be actuatable between a first position and a second position with the actuation member. The positioning and configuration of the spacer may allow a user to adjust the depth to which a drill bit may be able to drill into or through a bone when advanced through the lumen of the guide member after positioning the drill bit in the lumen and without completely withdrawing the drill bit from the lumen to make adjustments to the depth that the drill bit may be advanced from the second end of the guide member (e.g., the depth that the drill bit may be advanced into or through the bone).

In some illustrative instances, the apparatus for guiding medical instruments used in attaching a bone plate to a bone of a patient may include a handle assembly, a guide member, a locking mechanism, an actuatable spacer, and an actuation member configured to actuate the actuatable spacer between a first position and a second position. The guide member may extend from the handle assembly and the spacer may be operatively coupled to the handle assembly, where the actuation member may be operatively coupled to the spacer. Actuation of the actuation member may adjustably position the spacer in the first position adjacent the first end of the guide member and/or in one or more second positions spaced from the guide member. The locking mechanism may lock the spacer in the first position and/or in one or more of the second positions.

In some instances, the apparatus for guiding medical instruments used in attaching a bone plate to a bone of a patient may be utilized in a method of adjusting a drill depth of a drill guide configured to guide a drill bit toward a bone. For example, the apparatus may include a guide member with a handle assembly that may be positioned adjacent a bone. An actuatable spacer operatively coupled to the guide member may be positioned in a first position adjacent the first end of the guide member to limit the extent a drill bit can extend from the second end of the guide member to a first depth. The actuation member may be actuated to actuate the spacer to a second position spaced from the first end of the guide member while remaining operatively coupled to the guide member to limit the extent a drill bit can extend from the second end of the guide member to a second depth greater than the first depth.

The above summary of some example aspects is not intended to describe each disclosed embodiment or every implementation of the claimed disclosure.

BRIEF DESCRIPTION OF THE DRAWINGS

The disclosure may be more completely understood in consideration of the following detailed description of various embodiments in connection with the accompanying drawings, in which.

Figure 1:
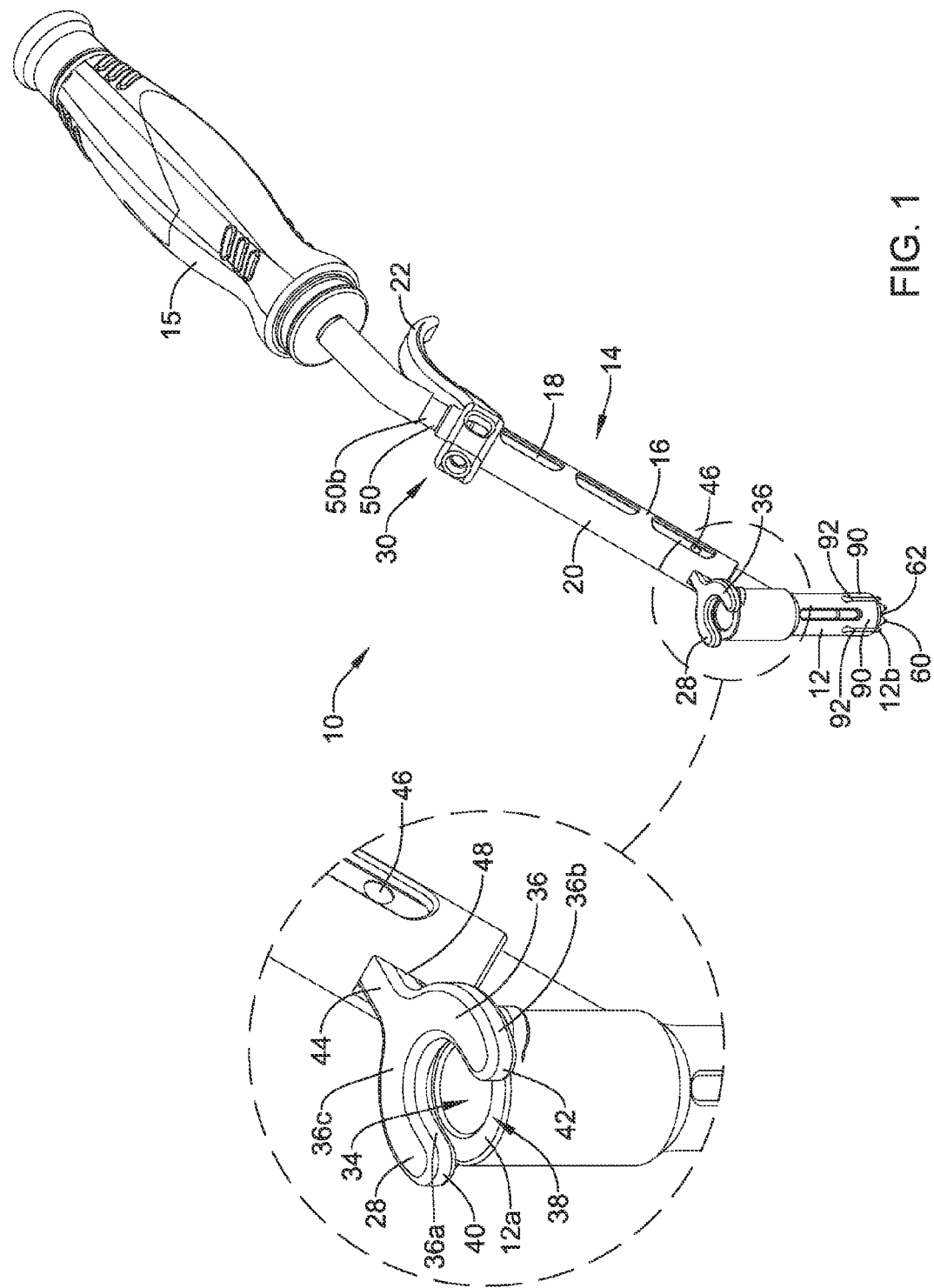
FIG. 1 is a schematic perspective view of an illustrative apparatus for guiding medical instruments according to an aspect of the disclosure.

While the disclosure is amenable to various modifications and alternative forms, specifics thereof have been shown by way of example in the drawings and will be described in detail. It should be understood, however, that the intention is not to limit aspects of the claimed disclosure to the particular embodiments described. On the contrary, the intention is to cover all modifications, equivalents, and alternatives falling within the spirit and scope of the claimed disclosure.

DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

As used herein, the proximal end (i.e., trailing end) of an object is the end that is closest to the individual or instrument inserting the object during a medical procedure and the distal end (i.e., leading end) of an object is the end that is farthest from the individual or instrument inserting the object during a medical procedure.

As used herein, any numerical or other order designations of elements (e.g., first, second, third, a, b, c, etc.) are used for descriptive purposes to improve the clarity of the description of the disclosure and differentiate between similar disclosed features. These numerical indications, unless expressly indicated, are not used for any limiting purposes.

The following detailed description should be read with reference to the drawings in which similar elements in different drawings are numbered the same. The detailed description and the drawings, which are not necessarily to scale, depict illustrative embodiments and are not intended to limit the scope of the claimed disclosure. The illustrative embodiments depicted are intended only as exemplary. Selected features of any illustrative embodiment may be incorporated into an additional embodiment unless clearly stated to the contrary.

Turning to the figures, FIGS. 1-7 depict various views of an illustrative apparatus or guide device 10, which are provided merely for the purpose of illustrating features disclosed herein.

Referring to FIG. 1, a guide device 10 is depicted having a guide member 12 with a handle assembly 14 extending therefrom to a handle 15. The handle assembly 14 may include a handle shaft 16 extending from the guide member 12 to the handle 15 and an actuation member 22 extending from the handle shaft 16 or otherwise arranged with the handle assembly 14. The guide device 10 may include a spacer 28 that may be adjustably connected to the handle assembly 14 and/or guide member 12, and selectably positionable adjacent the guide member 12. In some instances, a locking mechanism 30 may communicate with the handle shaft 16 and/or the actuation member 22 to adjustably secure the spacer 28 in one of a plurality of positions.

The guide member 12 may be formed (e.g., monolithically or otherwise) with one or more components of the handle assembly 14. Alternatively, the guide member 12 may be connected to one or more components of the handle assembly 14 in any manner including, but not limited to, a snap connection, a cam and strap connection, a bayonet connection, weld, threaded fastener(s), etc. The guide member 12 may include a first end 12a (e.g., a proximal end) and a second end 12b (e.g., a distal end) with a lumen 34 extending through the guide member 12 from the first end 12a to the second end 12b (see FIGS. 6 and 7). The lumen 34 may receive a screw, a drill bit, a drill, a tap, a probe, or other feature to facilitate connecting a bone plate 24 (e.g., a cervical plate, an occipital plate, or other plate) to a bone of a patient. In some instances, the guide member 12 may be used to prepare a bone for receiving a bone screw, such as a bone screw used to secure a bone plate 24 to a bone of a patient, or a pedicle screw or other bone screw used to secure another spinal construct to a bone of a patient.

In some cases, the spacer 28 may be positioned adjacent the first end 12a of the guide member 12 when at a first position such that an opening through the spacer 28 is aligned with the lumen 34 of the guide member 12 to effectively extend the lumen 34 to the proximal end of the spacer 28. In one example, the first end 12a of the guide member 12 may be substantially flat to receive the spacer 28 against the flat proximal end of the guide member 12 when positioned in the first position, as shown in FIG. 1. In other words, in some instances the spacer 28 may be positionable against the flat proximal end 12a of the guide member 12 in the first position. In other examples, the first end 12a of the guide member 12 may be flat or substantially flat, and/or include one or more spacer and/or drill receiving features, (e.g. one or more projections, one or more snap connectors, one or more indentations, etc.). The second end 12b of the guide member 12 may include one or more peaks 60 between valleys 62 or other gripping or engaging features, such as bone engaging features.

In some embodiments, the spacer 28 may be pivotable relative to the guide member 12 such that the spacer 28 may be pivoted between a first position adjacent the first end 12a of the guide member 12 and a second position away from the first end 12a of the guide member 12. In some instances, the spacer 28 may pivot about an axis perpendicular to the central longitudinal axis of the lumen 34 of the guide member 12, the spacer 28 may pivot about an axis parallel to the central longitudinal axis of the lumen 34 of the guide member 12, or the spacer 28 may pivot about another axis transverse to the central longitudinal axis of the lumen 34 of the guide member, for example.

The handle shaft 16 may include a first elongate member 18 (e.g., an inner shaft) and a second elongate member 20 (e.g., an outer sleeve) actuatable relative to the first elongate member 18. For example, the second elongate member 20 may be configured to move in a longitudinal direction relative to the first elongate member 18 through actuation of the actuation member 22. In some instances, the inner shaft or first elongate member 18 may be fixed to the guide member 12 while the outer sleeve or second elongate member 20 may be actuatable (e.g., longitudinally or rotatably actuatable) relative to the guide member 12 and the first elongate member 18. In other instances, the second elongate member 20 may be fixed to the guide member 12 while the first elongate member 18 may be actuatable (e.g., longitudinally or rotatably actuatable) relative to the guide member 12 and the second elongate member 20.

The first elongate member 18 (e.g., inner shaft) may engage or otherwise may be in communication with the spacer 28 (e.g., the spacer 28 may be adjustably connected to the first elongate member 18). For example, the spacer 28 may be pivotably connected to the first elongate member 18 via a pin or post 46. The second elongate member 20 (e.g., outer sleeve) may be positioned along the first elongate member 18, such as concentrically positioned about the first elongate member 18 (e.g., inner shaft) in some instances. In other embodiments, the second elongate member 20 may be positioned beside the first elongate member 18 or through the first elongate member 18, or otherwise positioned along the first elongate member 18, if desired. In some instances, the inner shaft or first elongate member 18 may be able to move axially within the outer sleeve or second elongate member 20 and/or the outer sleeve or second elongate member 20 may be able to move axially about the inner shaft or first elongate member 18. Such movement may accordingly adjust a position of the spacer 28 with respect to the first end 12a of the guide member 12. In one example, actuation of the outer sleeve or second elongate member 20 in a first direction D (shown in FIG. 7) relative to the guide member 12 and the inner shaft or first elongate member 18 may actuate the spacer 28 toward the first position of the spacer 28 adjacent the first end 12a of the guide member 12, and actuation of the outer sleeve or second elongate member 20 in a second direction D' (shown in FIG. 7) relative to the guide member 12 and the inner shaft or first elongate member 18 may actuate the spacer 28 toward the second position (e.g., spaced away from the first end 12a of the guide member 12).

The actuation member 22 of the handle assembly 14 may be actuated to adjust the position of the outer sleeve or second elongate member 20 with respect to the inner shaft or first elongate member 18. The actuation member 22 may take on any shape and size. In some instances, the shape and/or size of the actuation member 22 may be configured to facilitate adjustment of the actuation member 22. In one example, as shown in FIGS. 1-7, the actuation member 22 may have a rounded shape or partial C-shape that may be configured to receive a user's finger. In other examples, the actuation member 22 may have an S-shape that may be configured to receive two fingers of a user, where a first curved portion may be configured to receive a force from a finger in substantially the second direction D' and a second curved portion may be configured to receive force from a finger in substantially the first direction D opposite the second direction D'. In other embodiments, the actuation member 22 may be a loop for receiving a finger of a user, or the actuation member 22 may be a lever, knob, button or other mechanism for effecting actuation of the second elongate member 20 relative to the first elongate member 18. In the illustrated embodiment, the actuation member 22 may be fixed to the outer sleeve or second elongate member 20 such that the second elongate member 20 moves with the actuation member 22.

The actuation member 22 may be in communication with the locking mechanism 30 and the spacer 28. For example, when a force is applied to the actuation member 22 in the first direction D, the actuation member 22, the locking mechanism 30, and the outer sleeve or second elongate member 20 may move with respect to the inner shaft or first elongate member 18 (or, the inner shaft or first elongate member 18 may move with respect to the actuation member 22, the locking mechanism 30, and the outer sleeve or second elongate member 20). Such movement may adjust the spacer 28 from a second position spaced from the first end 12a of the guide member 12 to a first position adjacent the first end 12a of the guide member 12. In the example, when a force is applied to the actuation member 22 in the second direction D', the actuation member 22, the locking mechanism 30, and the outer sleeve or second elongate member 20 may move with respect to the inner shaft or first elongate member 18 (or, the inner shaft or first elongate member 18 may move with respect to the actuation member 22, the locking mechanism 30, and the outer sleeve or second elongate member 20), where such movement may adjust the spacer 28 from the first position adjacent the first end 12a of the guide member 12 to the second position spaced from the first end 12a of the guide member 12.

In some instances, the actuation member 22, the locking mechanism 30, and the outer sleeve or second elongate member 20 may be at least partially monolithically formed. In other instances, one or more of the actuation member 22, the locking mechanism 30, and the outer sleeve or second elongate member 20 may be formed separate from one or more of the actuation member 22, the locking mechanism 30, and the outer sleeve or second elongate member 20 and connected in any manner.

In some illustrative instances, the guide device 10 may be formed from substantially three parts. For example, the first part may include the spacer 28, the second part may include the guide member 12 monolithically formed with the inner shaft or first elongate member 18, and the third part may include the monolithically formed actuation member 22, outer sleeve or second elongate member 20, and optionally the locking mechanism 30. A handle 15, which may be permanently attached to the first elongate member 18, or removably attached to the first elongate member (e.g., with a quick attachment mechanism) may also be provided. In the example, the inner shaft or first elongate member 18 of the second part may be inserted into the outer sleeve or second elongate member 20 of the third part, and the spacer 28 of the first part may be inserted through the outer sleeve or second elongate member 20 of the third part and connected to the inner shaft or first elongate member 20 of the second part.

Figure 2:
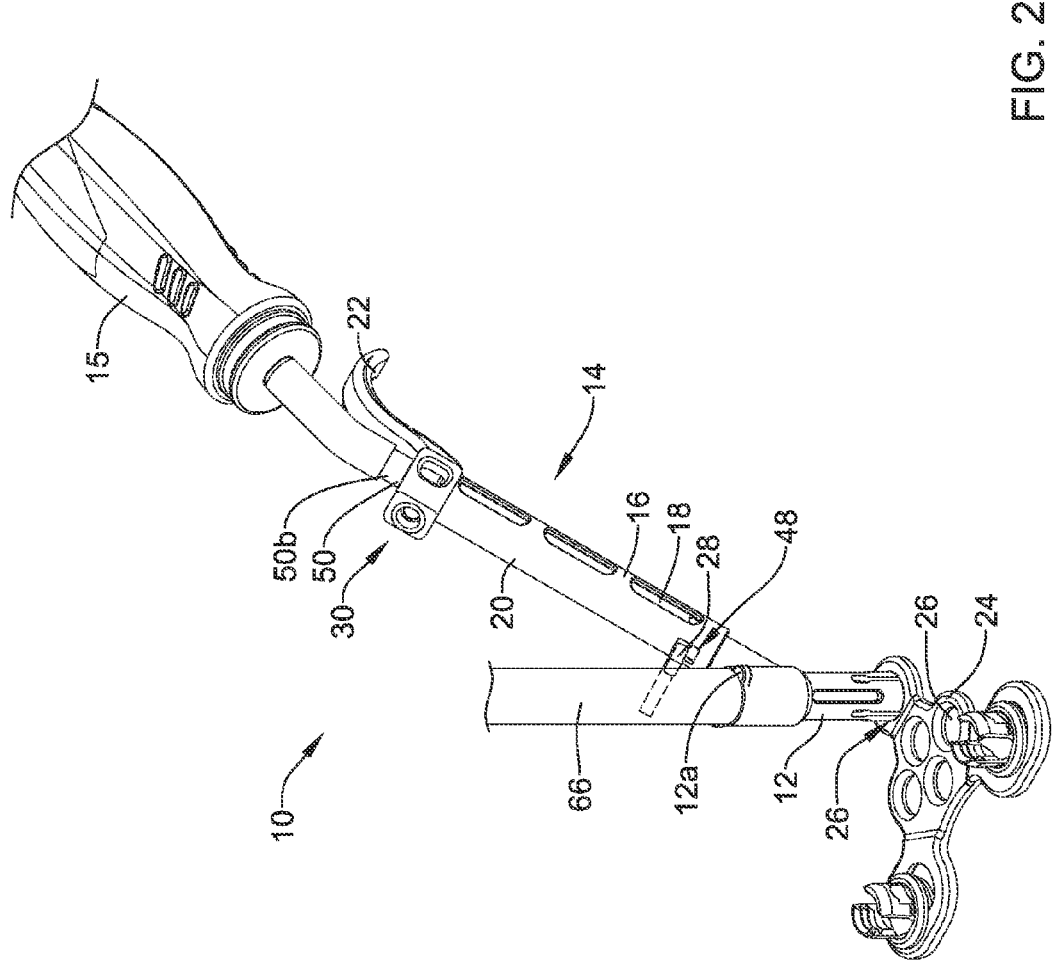
FIG. 2 is a schematic perspective view of an illustrative apparatus for guiding medical instruments according to an aspect of the disclosure interacting with an illustrative bone plate.

As shown in FIG. 2, the guide device 10 may be used with a bone plate 24 (e.g., an occipital plate, a cervical plate or other spinal plate, or other bone plate). In some instances, the guide device 10 may facilitate attaching the plate 24 to a skull bone (e.g., occipital bone) and/or a vertebral body. In general, plates 24 are known in the art and may be configured to be affixed to a skull bone and/or a vertebral body via bone screws. In one example, the plate 24 may include one or more bone screw receiving holes 26, as shown in FIG. 2. The second end 12b of the guide member 12 may be configured to fit into and/or mate with the bone screw holes 26 of the bone plate 24. Illustratively, cervical plates or occipital plates may represent two of several different types, sizes, and configurations of plates 24. Various illustrative cervical plates are described in greater detail in U.S. Pat. Nos. 6,193,721; 6,398,783; 6,416,528; 6,454,771; and D449,692; the contents of which are incorporated by reference herein in their entirety. Various illustrative occipital plates are described in greater detail in U.S. Pat. Nos. 8,246,662; 8,337,496; 8,147,527; 8,007,449; and 7,621,942; the contents of which are incorporated by reference herein in their entirety.

Figure 3A:
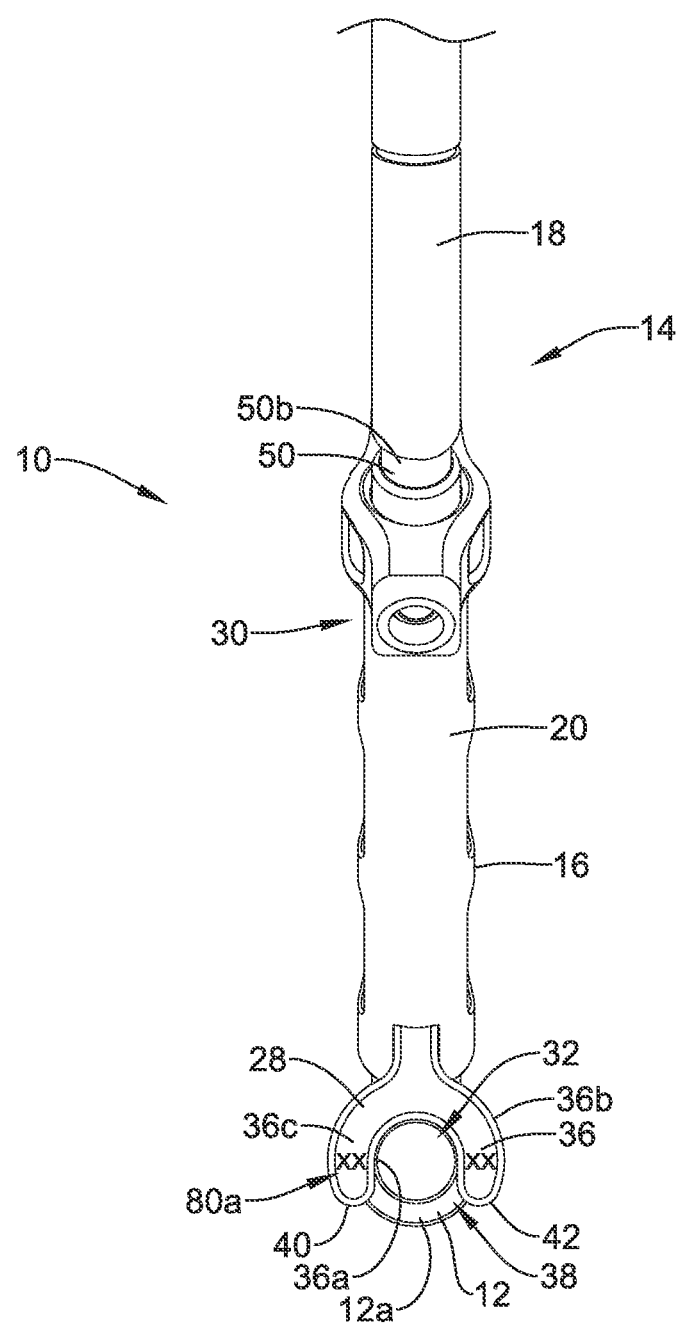
FIG. 3A is a schematic top view of an illustrative apparatus for guiding medical instruments according to an aspect of the disclosure, where an illustrative spacer is in a first position.
Figure 3B:
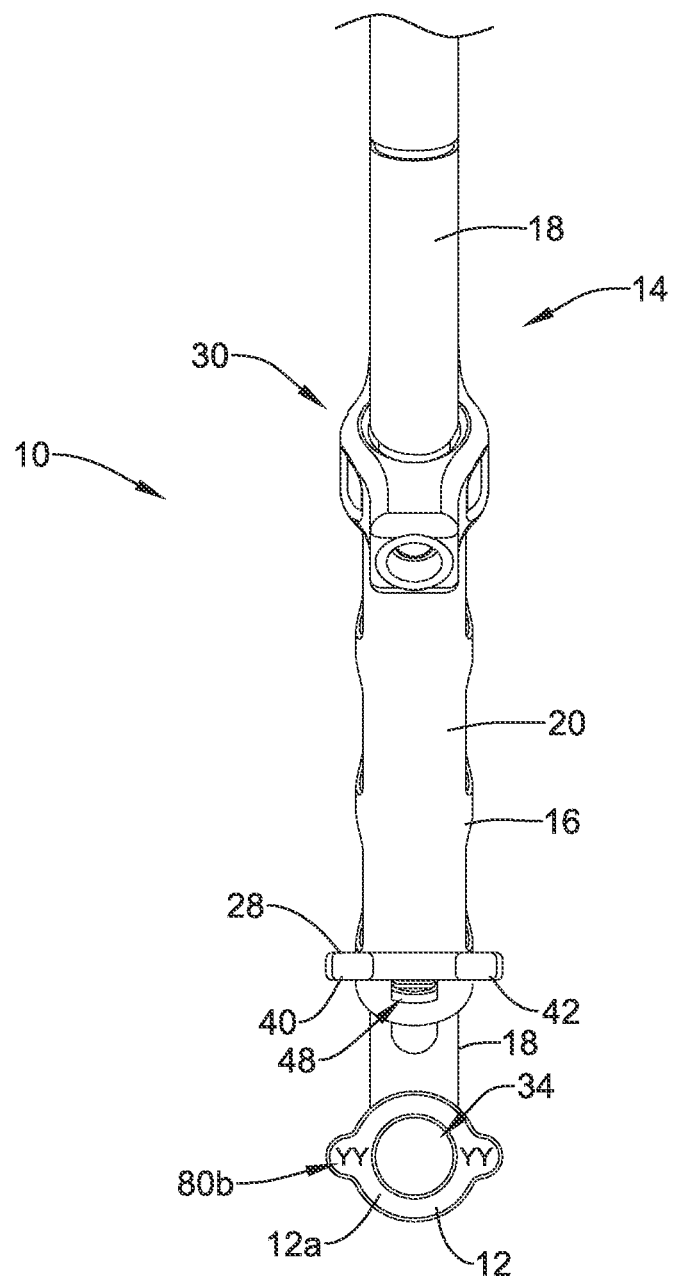
FIG. 3B is a schematic top view of an illustrative apparatus for guiding medical instruments according to an aspect of the disclosure, where an illustrative spacer is in a second position.

FIGS. 3A and 3B are schematic top views of the guide device 10 with the spacer 28 in the first position (as shown in FIG. 3A) and with the spacer 28 in the second position (as shown in FIG. 3B). As can be seen from the top view of the guide device 10 with the spacer 28 in the first position, the spacer 28 may include a through hole 32 extending therethrough. Illustratively, the through hole 32 may receive a drill bit of a drill and/or a tap and/or other feature to facilitate attaching the plate 24 to a patient. The through hole 32 of the spacer 28 may align with a lumen 34 extending through the guide member 12 when the spacer 28 is in the first position (e.g., the through hole 32 of the spacer 28 may axially align with a central longitudinal axis of the lumen 34 or otherwise be in alignment with any other axis extending through the lumen 34). The through hole 32 of the spacer 28 and the lumen 34 may align such that a drill bit of a drill, a tap, or other feature extending at least partially through the through hole 32 may also extend at least partially through the lumen 34 of the spacer 28.

The spacer 28 may include a perimeter portion 36 that at least partially defines the through hole 32. The perimeter portion 36 of the spacer 28 may include an inner edge 36a and an outer edge 36b and the intermediate material 36c, if any, between the inner edge 36a and the outer edge 36b. In addition to defining the through hole 32 of the spacer 28, the perimeter portion 36 may at least partially define an opening 38 in the spacer 28 extending from the through hole 32 to the outer perimeter 36b transverse to the longitudinal axis of the through hole 32. The opening 38 of the spacer 28 may be entirely or at least partially defined by a first end 40 and a second end 42 of the perimeter portion 36. The opening 38 may facilitate allowing the spacer 28 to move from a first position adjacent the first end 12a of the guide member 12 to a second position spaced from the first end 12a of the guide member 12 while a drill bit, a tap, and/or other feature is extending at least partially into or through the through hole 32 and/or extending into or through the lumen 34 of the guide member 12. For example, the distance or gap between the first end 40 and the second end 42 may be larger than the diameter of a drill bit or tap extending through the through hole 32 and/or extending into or through the lumen 34 of the guide member 12 such that the drill bit or tap may pass out of the hole 32 in a direction transverse to the longitudinal axis of the hole 32 and the drill bit or tap.

Figure 4:
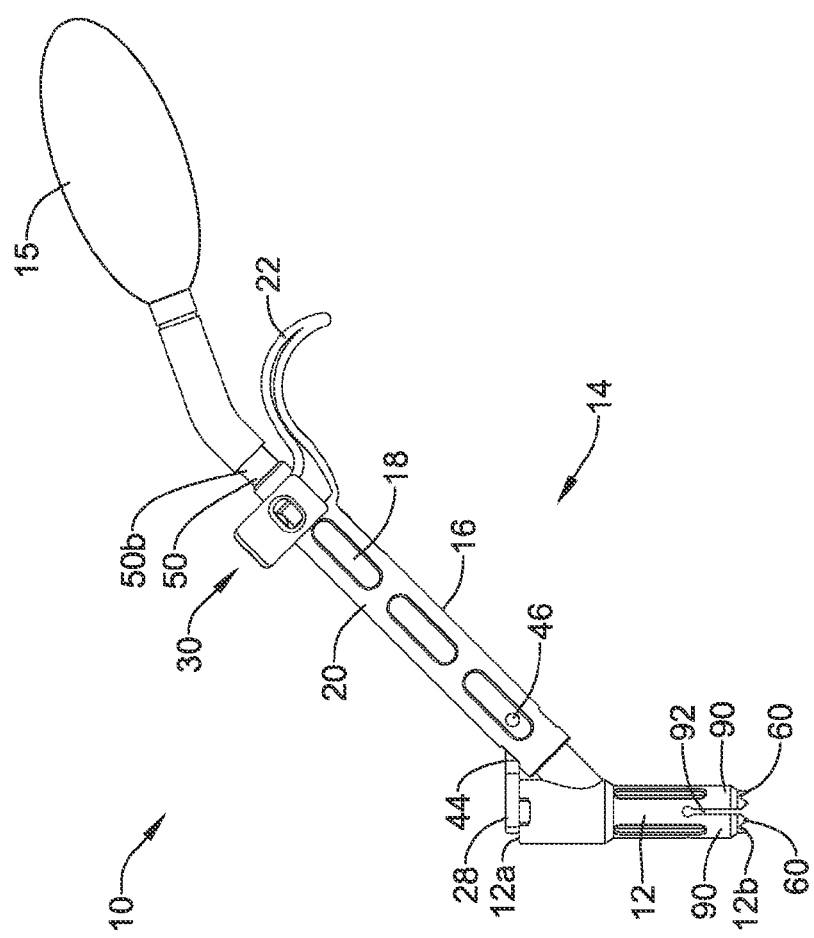
FIG. 4 is a schematic side view of an illustrative apparatus for guiding medical instruments according to an aspect of the disclosure.

FIG. 4 is a schematic side view of the guide device 10. As can be seen from the side of the guide device 10, the spacer 28 may extend into the handle shaft 16 and may engage the inner shaft or first elongate member 18 of the handle shaft 16 (see FIGS. 6 and 7). The spacer 28 may engage the inner shaft or first elongate member 18 in a manner that allows the spacer 28 to move from the first position adjacent the guide member 12 to the second position spaced from the guide member 12 and vice versa. For example, the spacer 28 may pivot between the first position and the second position about a pivot axis. For example, a pin or post 46 may pivotably attach the spacer 28 to the inner shaft or first elongate member 18. Illustratively, a tongue 44 of the spacer 28 may extend into the handle shaft 16 and a pin 46 may extend through the tongue 44 and engage the inner shaft or first elongate member 18 to permit the spacer 28 to pivot in an adjustable manner (e.g., in a pivotable manner). In some instances, the pin 46 may be press fit into a bore of the inner shaft or first elongate member 18 such that the spacer 28 may pivot or rotate relative to the pin 46. In other instances, the pin 46 may be formed with or fixed to (e.g. press fit) the spacer 28 such that the pin 46 may pivot or rotate relative to the inner shaft or first elongate member 18.

Figure 5:
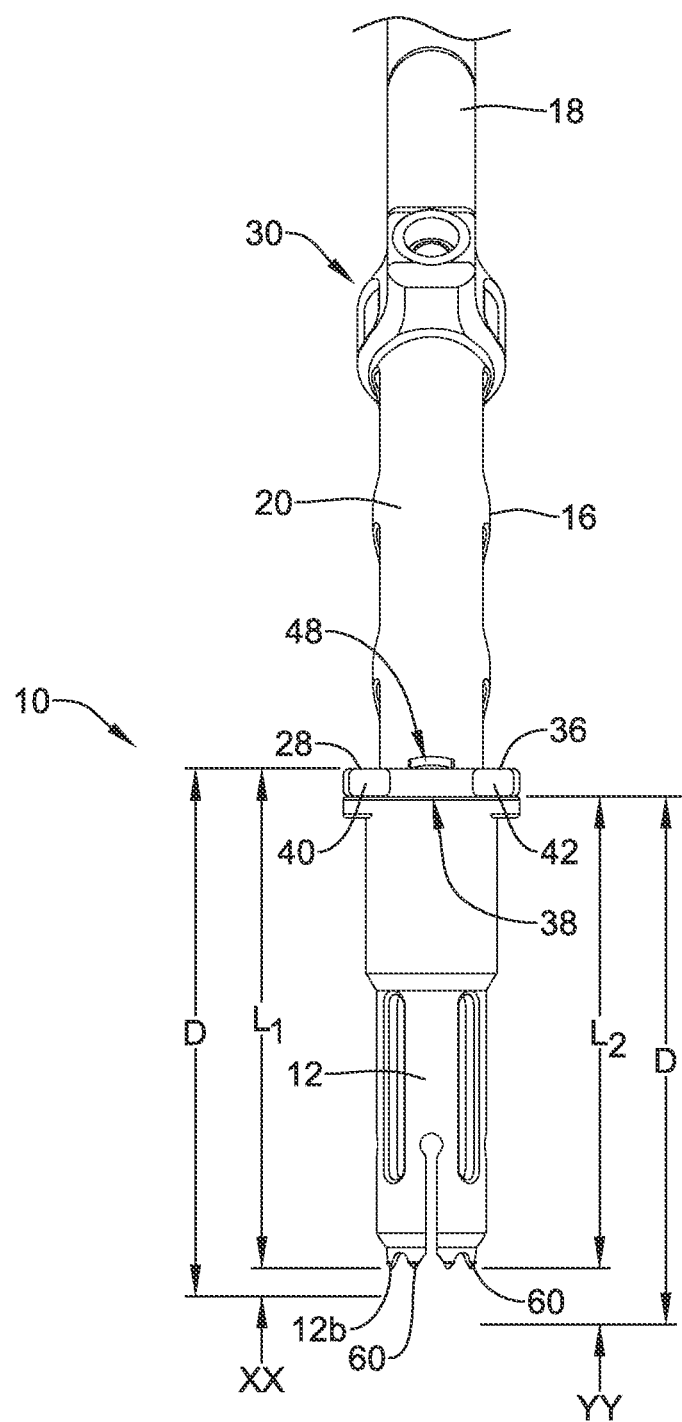
FIG. 5 is a schematic front view of an illustrative apparatus for guiding medical instruments according to an aspect of the disclosure.

FIG. 5 is a schematic front view of the guide device 10. As can be seen from the front of the guide device 10, the guide member 12 combined with the spacer 28 may have a first length $L_1$ (e.g., when the spacer 28 is in the first position, as in FIG. 5) and the guide member 12 (e.g., when the spacer 28 is in the second position, as in FIG. 2) may have a second length $L_2$ less than $L_1$. Accordingly, the difference between the first length $L_1$ with the spacer 28 in the first position and the second length $L_2$ with the spacer 28 in the second position may be equivalent to the thickness of the spacer 28 measured from the distal surface of the spacer 28 facing the proximal end 12a of the guide member 12 to the proximal surface of the spacer 28 opposite the distal surface.

A drill bit (or tap) having a working length D (i.e., the length of the drill bit permitted to be passed through the lumen 34 of the guide member 12, such as the length of the drill bit from a stop to the distal tip of the drill bit) extending distally from the proximal side of the spacer 28 may be able to extend from the distal end 12b of the guide member 12 a maximum distance XX with the spacer 28 in the first position. When the spacer 28 is actuated to the second position, the drill bit (or tap) may be able to extend from the distal end 12b of the guide member 12 a maximum distance YY greater than the maximum distance XX, allowing the drill bit (or tap) to extend further from the distal end 12b of the guide member 12. In some instances, the spacer 28 may provide a differential between the maximum distance XX and the maximum distance YY of 1 millimeter, 2 millimeters, 3 millimeters, or other desired difference in maximum depth the drill bit may attain.

Accordingly, a user is able to control the maximum distance the drill bit is permitted to extend from the distal end 12b of the guide member 12 (e.g., the maximum depth the drill bit is permitted to drill into a bone of a patient when the stop or drill head of the drill abuts the first end 12a of the guide member 12 with the spacer 28 in the second position and when the stop or drill head of the drill abuts the spacer 28 with the spacer 28 in the first position. Such knowledge may allow a user to drill to a first depth XX and then if it is determined it is necessary to drill deeper, the user may adjust the spacer 28 and further drill to a second depth YY that is deeper than the first depth XX without completely removing the drill bit from the guide member 12. In some instances, the first depth XX may be 6 millimeters while the second depth YY may be 8 millimeters, the first depth XX may be 8 millimeters while the second depth YY may be 10 millimeters, the first depth XX may be 10 millimeters while the second depth YY may be 12 millimeters, the first depth XX may be 12 millimeters while the second depth YY may be 14 millimeters, or the first depth XX may be 14 millimeters while the second depth YY may be 16 millimeters, for example.

In some instances, the guide member 12 may have indicia 80b (shown in FIG. 3B) located at the first or proximal end 12a and/or indicia located at another location. Illustratively, the indicia 80b may indicate the maximum distance YY within a patient (e.g., depth) in which a drill bit (configured to be used with the guide device 10) will extend from the distal end 12b of the guide member 12 when the drill powering the drill bit or an associated stop on the drill or drill bit abuts the first end 12a of the guide member 12 with the spacer 28 in the second position. For example, the indicia 80b may indicate the greatest extent the drill bit will extend from the second end 12b of the guide member 12 when the drill bit is fully advanced into the lumen 34 of the guide member 12 with the spacer 28 in the second position. Such indicia may allow a physician to observe and determine the maximum depth of the bore drilled into the bone during a medical procedure with the spacer 28 in the second position.

The spacer 28 may also have indicia 80a (shown in FIG. 3A) located at the proximal end of the spacer 28, or at another location. Illustratively, the indicia 80a may indicate the maximum distance XX within a patient (e.g., depth) in which the drill bit (configured to be used with the guide device 10) will extend from the distal end 12b of the guide member 12 when the drill powering the drill bit or an associated stop on the drill or drill bit abuts the proximal end of the spacer 28 with the spacer in the first position. For example, the indicia 80a may indicate the greatest extent the drill bit will extend from the second end 12b of the guide member 12 when the drill bit is fully advanced into the lumen 34 of the guide member 12 with the spacer in the first position. Such indicia may allow a physician to observe determine the maximum depth of the bore drilled into the bone during a medical procedure with the spacer 28 in the first position.

The indicia 80a located at the proximal side of the spacer 28 when in the first position may be visible to the user, while the spacer 28 may cover the indicia 80b on the proximal end 12a of the guide member 12, and thus not visible to the user. When the spacer 28 is actuated to the second position (e.g., pivoted away from the first end 12a of the guide member 12), the indicia 80b on the proximal end 12a of the guide member 12 may be uncovered and become visible to the user and the indicia 80a on the spacer 28 may be out of view of the user.

Figure 6:
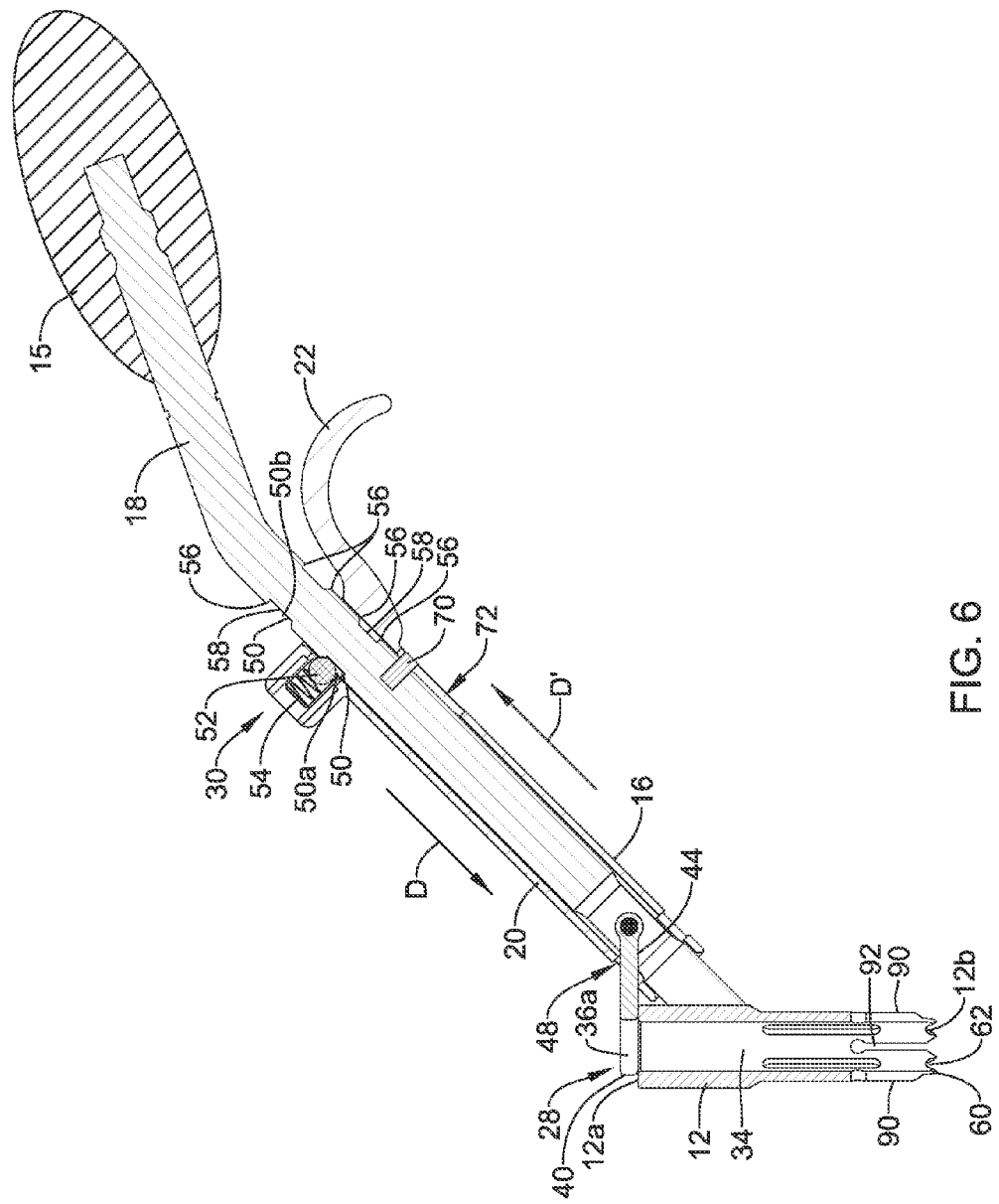
FIG. 6 is a schematic cross-sectional view of an illustrative apparatus for guiding medical instruments according an aspect of the disclosure, with a spacer in a first position.

FIG. 6 is a schematic cross-sectional side view of the guide device 10, where the spacer 28 is in the first position adjacent the first end 12a of the guide member 12. The actuation member 22 and the locking mechanism 30 are also shown illustratively in respective first positions with respect to the inner shaft or first elongate member 18.

Figure 7:
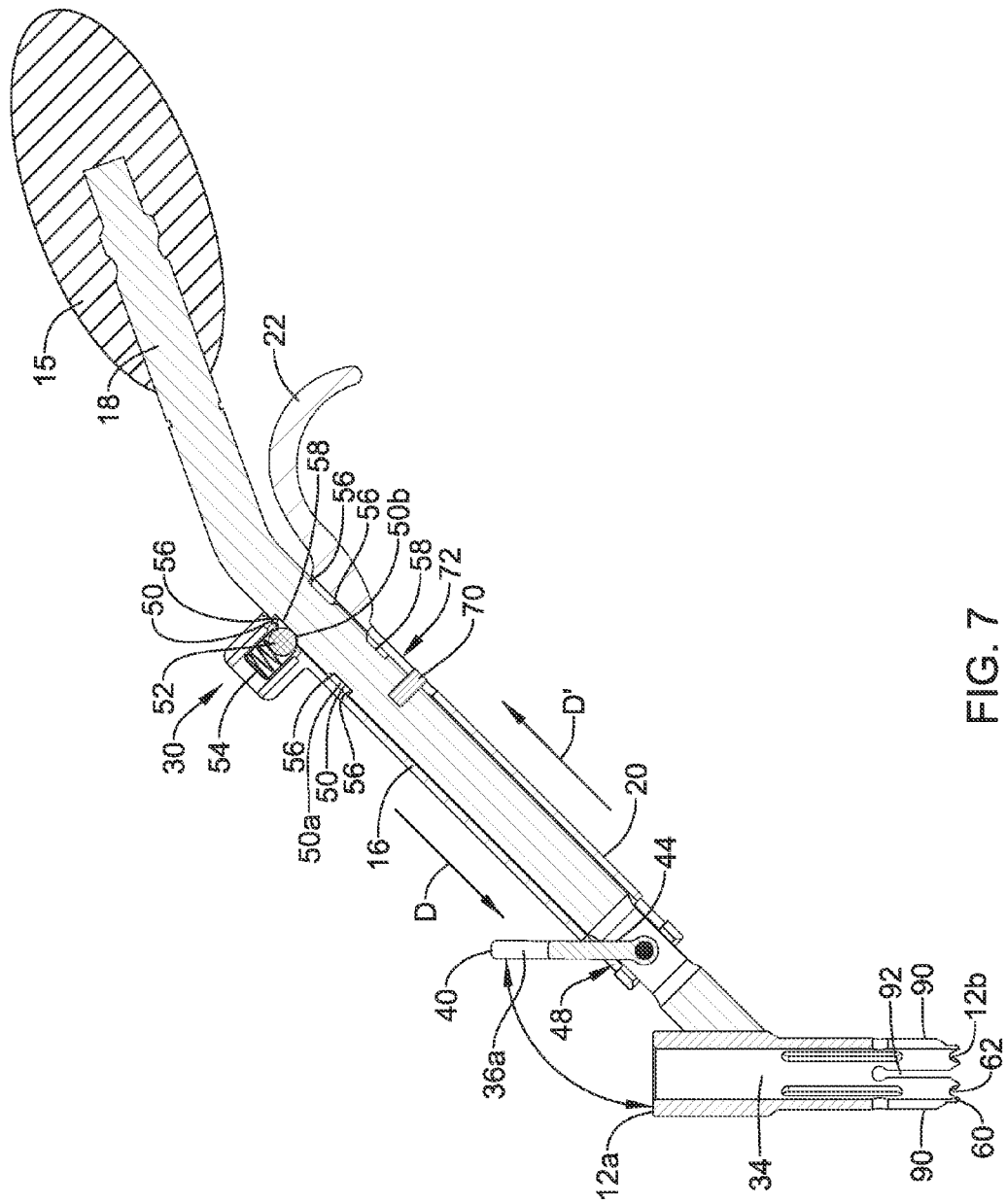
FIG. 7 is a schematic cross-sectional view of an illustrative apparatus for guiding medical instruments according to an aspect of the disclosure, with a spacer in a second position.

FIG. 7 is a schematic cross-sectional side view of the guide device 10, where the spacer 28 is in the second position spaced from the first end 12a of the guide member 12. The actuation member 22 and the locking mechanism 30 are also shown illustratively in respective second positions with respect to the inner shaft or first elongate member 18.

As shown in FIGS. 6 and 7 and discussed above, the handle shaft 16 may include a first elongate member 18 (e.g., inner shaft) and second elongate member 20 (e.g., outer sleeve), wherein the inner shaft or first elongate member 18 and the outer sleeve or second elongate member 20 may be capable of axial movement with respect to one another. In some instances, the locking mechanism 30 may adjustably fix or lock the inner shaft 18 in an axial adjusted position with respect to the outer sleeve 20.

As shown in FIGS. 6 and 7, the tongue 44 of the spacer 28 may extend through an opening 48 in the outer sleeve or second elongate member 20 of the handle shaft 16 and may abut an edge of the opening 48. As a result of the spacer 28 extending through the opening 48 in the outer sleeve or second elongate member 20 and adjustably engaging the inner shaft or first elongate member 18 of the handle shaft 16, the position of the spacer 28 with respect to the first end 12a of the guide member 12 may move in response to axial movement of the outer sleeve or second elongate member 20 relative to the inner shaft or first elongate member 18 and the guide member 12.

In some examples, the outer sleeve or second elongate member 20 and actuation member 22 may actuate (e.g., axially or in any other manner) from a first locked position (e.g., a first position), as shown in FIG. 6, to a second locked position (e.g., a second position), as shown in FIG. 7. The locking mechanism 30 may engage a lock receiver 50 (e.g., a first lock receiver 50a or a second lock receiver 50b) to lock the spacer 28, the locking mechanism 30, and/or the actuation member 22 in the first position and/or the second position. In one example, the lock receivers 50 may be indentations or detents in the inner shaft or first elongate member 18, as shown in FIGS. 1-7. However, the lock receivers 50 may be any type of engagement mechanism capable of receiving a lock and releasably securing the spacer 28 in a position.

In some instances, a pin 70 may extend from the inner shaft or first elongate member 18 and extend through a pin opening 72 in the outer sleeve or second elongate member 20. The pin 70 may be integrally formed with the inner shaft or first elongate member 18 or connected to the first elongate member 18 in any manner. The pin 70 may interact with the pin opening 72 to limit axial movement and/or rotational movement of the inner shaft or first elongate member 18 and the outer sleeve or second elongate member 20 with respect to one another. In one example, the interaction between the pin 70 and the pin opening 72 may prevent axial movement of the inner shaft or first elongate member 18 with respect to the outer sleeve or second elongate member 20 of a distance greater than a distance between the outer extremes of the first lock receiver 50a and the second lock receiver 50b. Furthermore, the interaction between the pin 70 and the pin opening 72 may prevent rotational movement of the inner shaft or first elongate member 18 with respect to the outer sleeve or second elongate member 20. In some instances, the first and second elongate members 18, 20 may include complementary keying features to prevent rotational movement therebetween.

When the lock receivers 50 are indentations in the first elongate member 18, the lock receivers 50 may have sides 56 that are substantially perpendicular with a base 58 of the lock receivers 50, for example. Alternatively, one or more of the sides 56 may be at least partially chamfered, where the chamfered portion forms an angle with the base 58 that is less than ninety (90) degrees. In one example, one side 56 of the lock receivers 50 may be chamfered, as shown in the figures, to facilitate adjustment of the locking mechanism 30 and/or second elongate member 20 in the direction of the side 56 of the lock receivers 50 that is chamfered. For example, as shown in FIGS. 6 and 7, a distal lock receiver (e.g., the first lock receiver 50a) has a proximal side 56 that is chamfered and allows the locking mechanism 30 and/or the outer sleeve 20 to travel in a proximal direction in the direction of the chamfered side. In the example, a proximal lock receiver (e.g., the second lock receiver 50b) positioned proximal of the first lock receiver 50a has a distal side 56 that is chamfered and allows the locking mechanism 30 and/or the outer sleeve 20 to travel in a distal direction in the direction of the chamfered side.

The locking mechanism 30 may be any type of locking mechanism that may interact with the lock receivers 50 to adjustably set or lock the inner shaft or first elongate shaft 18 in an axial position with respect to the outer sleeve or second elongate shaft 20, as desired. As shown in FIGS. 6 and 7, the locking mechanism 30 may be a ball detent system, where a spherical mechanism 52 (e.g., a ball) is biased by a biasing mechanism 54 (e.g., a spring) toward a lock receiver 50 (e.g., a detent). Alternatively, or in addition, the locking mechanism may include a pin lock, a bayonet lock, or any other type of lock, if desired.

In some embodiments, the guide device 10 may include a plurality of spacers 28 that may be independently actuatable to adjust the maximum distance a medical device (e.g., a drill bit, a tap, a probe, etc.) may extend from the distal end 12b of the guide member 12. For example, the guide device 10 may include two or more spacers 28 pivotably coupled to the guide device 10. Accordingly, a first spacer 28 may be actuated between a first and second position to control the maximum depth of a medical device through the guide member 12 between first and second maximum depths. A second or additional spacer 28 may be independently actuated between a first and second position to further control the maximum depth of the medical device through the guide member 12. For example, in some instances, when both the first and second spacers 28 are both positioned in a first position, the medical device may be extended from the distal end 12b of the guide member 12 to a first maximum depth. When the first spacer 28 is actuated to the second position while retaining the second spacer 28 in the first position, the medical device may be extended from the distal end 12b of the guide member 12 to a second maximum depth greater than the first maximum depth. When both the first and second spacers 28 are positioned in the second position, the medical device may be extended from the distal end 12b of the guide member 12 to a third maximum depth greater than the first and second maximum depths. Additional spacers 28 may be provided to provide additional adjustment of the maximum depth a medical device may extend from the distal end 12b of the guide member 12.

In some instances, a distal end region of the guide member 12 may be configured to be removably coupled with the bone plate 24 to retain the bone plate 24 coupled thereto during use of the guide device 10. For example, in some instances the distal end region of the guide member 12 may frictionally fit into a bone screw opening 26 of a bone plate 24, or the distal end region of the guide member 12 may form an interference or interlocking fit with the bone plate 24 when the distal end 12b of the guide member 12 is inserted into or through the bone screw opening 26 of the bone plate 24.

Illustratively, the distal end region of the guide member 12 may include a plurality of prongs 90 extending to the distal end 12b of the guide member 12 as shown in FIG. 1. In some instances, a gap or slot 92 may be located between adjacent prongs 90. The gap or slot 92 may extend to the distal end 12b of the guide member 12. In the illustrated embodiment, the guide member 12 includes four prongs 90 and four gaps or slots 92 interposed between adjacent prongs 90. For example, the prongs 90 and slots 92 may be arranged symmetrically around the circumference of the guide member 12. However, in other embodiments the guide member 12 may include another number and/or arrangement of prongs 90, if desired.

Figure 8:
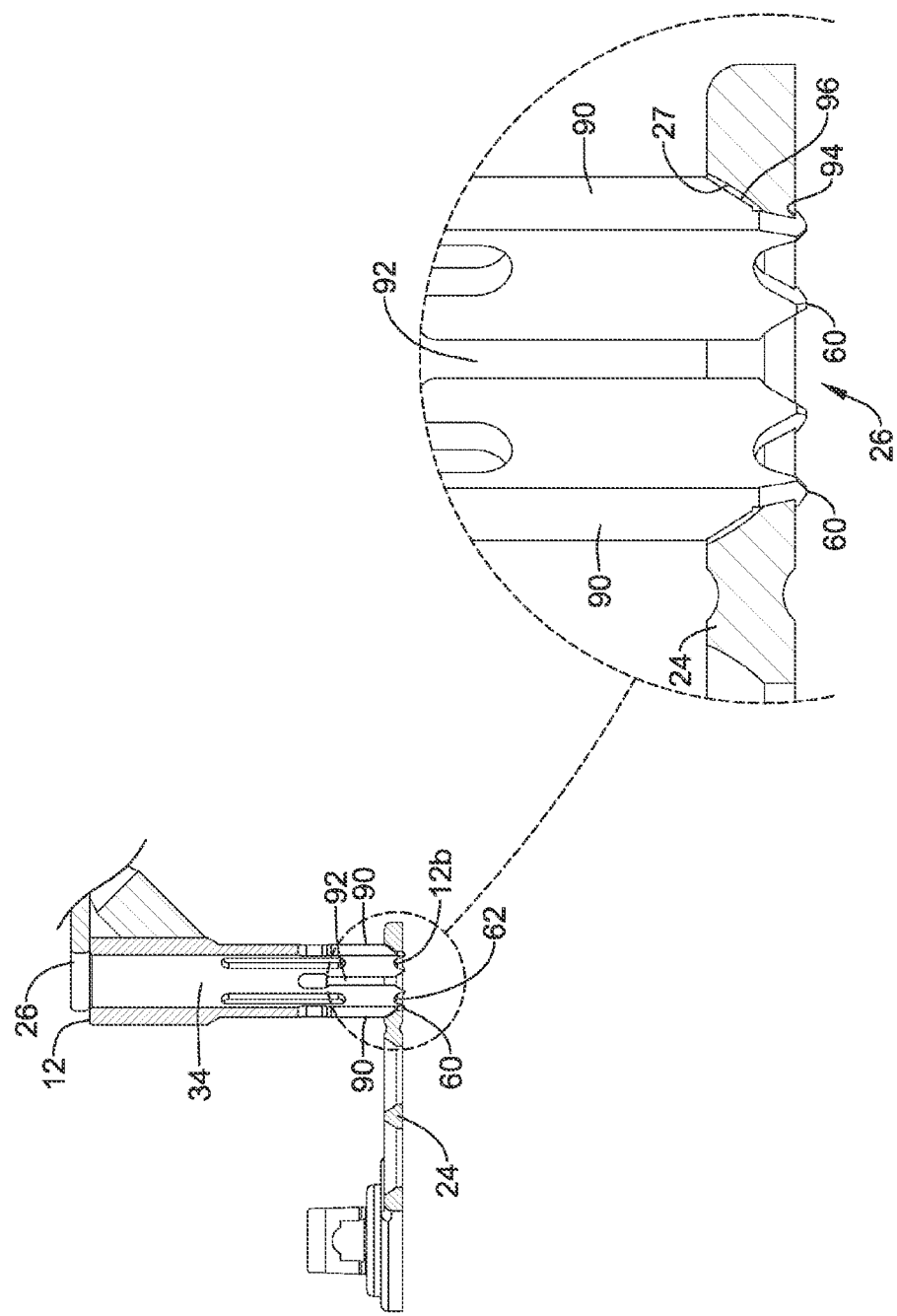
FIG. 8 is a cross-sectional view of the exemplary guide device engaged with a bone plate.

The prongs 90 may be configured to engage with the bone plate 24 when the distal end 12b of the guide member 12 is inserted into or through the bone screw opening 26 of the bone plate 24. For example, as shown in FIG. 8, one or more of the prongs 90 may include a lip or rim 94 configured to face a lower surface or edge of the bone plate 24 surrounding the bone screw opening 26 when the distal end 12b of the guide member 12 is inserted through the bone screw opening 26 from the upper surface of the bone plate 24. The rim or lip 94 may interlock with the bone plate 24, restricting disengagement of the guide member 12 from the bone plate 24. An annular groove may extend around the prongs 90 to form the rim or lip 94, and the bone plate 24 may extend into the annular groove when the guide member 12 is coupled to the bone plate 24. One or more of the prongs 90 may be able to flex or deflect relative to the other prongs 90 as the prongs 90 are inserted into the bone screw opening 26 to permit the rim or lip 94 of the prongs 90 to pass into and/or through the bone screw opening 26.

In some instances, the bone screw opening 26 may include a countersink region having a chamfered edge 27 configured to receive the head portion of a bone screw countersunk in the bone screw opening 26. The prongs 90 may include a beveled edge 96 configured to mate with or complement the chamfered edge 27 of the bone screw opening 26. Accordingly, the distal end 12b of the guide member 12 may be inserted through the bone screw opening 26 until the beveled edge 96 of the prongs 90 mates with and faces the chamfered edge 27 of the bone screw opening 26. The rim or lip 94 may contemporaneously engage a lower edge of the bone screw opening 26 to interlock the guide member 12 with the bone plate 24. When it is desired to disengage or decouple the guide member 12 from the bone plate 24, a sufficient force may be applied to the guide member 12 to cause the prongs 90 to deflect radially inwardly such that the rim or lip 94 can pass back proximally through the bone screw opening 26.

As can be seen in FIG. 8, the peaks 60 at the distal end 12b of the guide member 12 may extend distally beyond the lower surface of the bone plate 24 when the guide member 12 is interlocked with the bone plate 24 to engage a bone against which the bone plate 24 is positioned. The peaks 60 may help retain the bone plate 24 and the guide device 10 in a desired position against the bone during the medical procedure.

Figure 9:
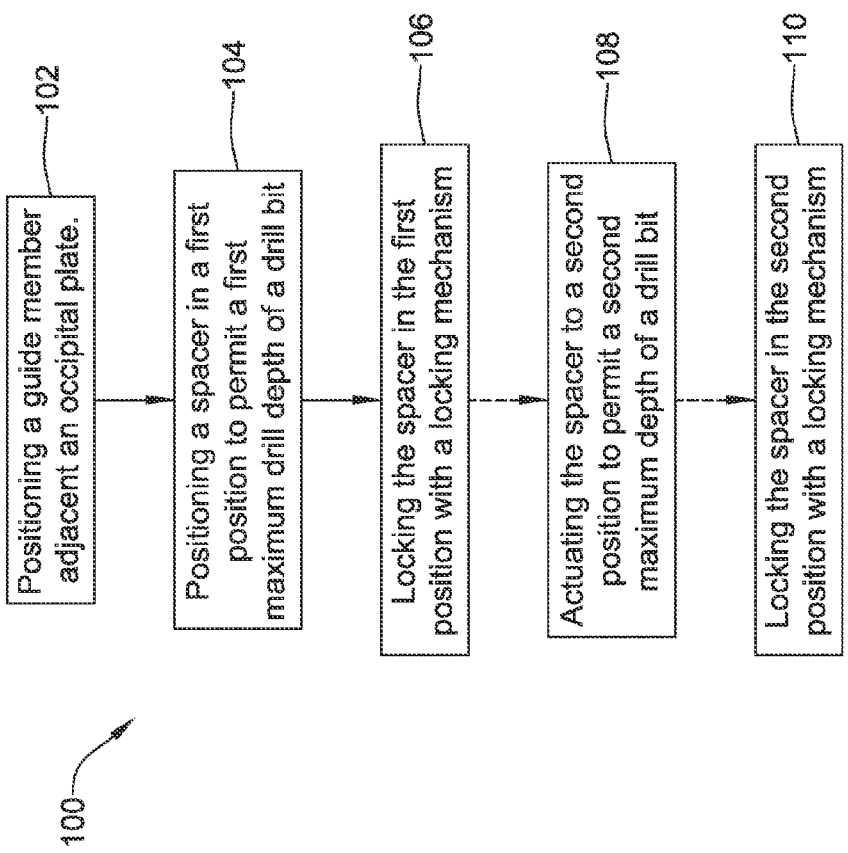
FIG. 9 is a schematic flow diagram of an illustrative method for adjusting a drill depth according to an aspect of the disclosure.

Illustratively, the guide device 10 may be used in a method 100 for controlling a maximum drill depth that a drill bit can be advanced into a bone of a patient, as shown in FIG. 9. For example, a user may position (step 102) a guide member 12 adjacent a bone plate 24. The guide member 12 may include a handle assembly 14 extending therefrom and a lumen 34 extending therethrough from a first end 12a to a second end 12b of the guide member 12. The user may position (step 104) a spacer 28 that that interacts with the guide member 12 in a first position adjacent the first end 12a of the guide member 12 to permit a first maximum drill depth of the drill bit extending through the lumen 34 of the guide member 12 (i.e., to permit a drill bit to extend from the distal end 12b of the guide member 12 a first maximum extent). When the spacer 28 is at the first position, the user may lock (step 106) the spacer 28 in the first position (e.g., permanently lock or adjustably lock) with a locking mechanism 30. As discussed above, the locking mechanism 30 may lock the spacer 28 at the first position in any locking manner, as desired.

Optionally, the user may position, such as reposition, (step 108) the spacer 28 in a second position to permit a second maximum drill depth of the drill bit extending through the lumen 34 of the guide member 12 (i.e., to permit the drill bit to extend from the distal end 12b of the guide member 12 a second maximum extent greater than the first maximum extent). When the spacer 28 is at the second position, the user may lock (step 110) the spacer 28 in the second position (e.g., permanently lock or adjustably lock) with a locking mechanism 30. As discussed above, the locking mechanism 30 may lock the spacer 28 at the second position in any locking manner, as desired.

To adjust the position of the spacer 28 into the first position adjacent the first end 12a of the guide member 12, the actuation member 22 may be adjusted. For example, the actuation member 22 may extend from the handle assembly 14 and a user may apply a force on the actuation member 22 in a second direction D' to unlock the locking mechanism 30 (e.g., if it is not already unlocked) and adjust the position of the actuation member 22 and adjust the spacer 28 to the second position from the first position, along with the positioning of the locking mechanism 30 and the outer sleeve or second elongate member 20 with respect to the inner shaft or first elongate member 18. Additionally, the actuation member 22 may extend from the handle assembly 14 and a user may apply a force on the actuation member 22 in the first direction D substantially opposite the second direction D' to unlock the locking mechanism 30 (e.g., if it is not already unlocked) and adjust the position of the actuation member 22 and adjust the spacer 28 to the first position from the second position, along with the position of the locking mechanism 30 and the outer sleeve or second elongate member 20 with respect to the inner shaft or first elongate member 18.

When installing a bone plate 24 to a bone 68, the guide device 10 may be coupled to the bone plate 24. For example, the distal end 12b of the guide member 12 may be inserted into and coupled to a bone screw opening 26 of the bone plate 24. The guide device 10 may then be used to guide a drill bit, a tap, or other instrument through the bone screw opening 26 during the installation procedure.

Figure 10:
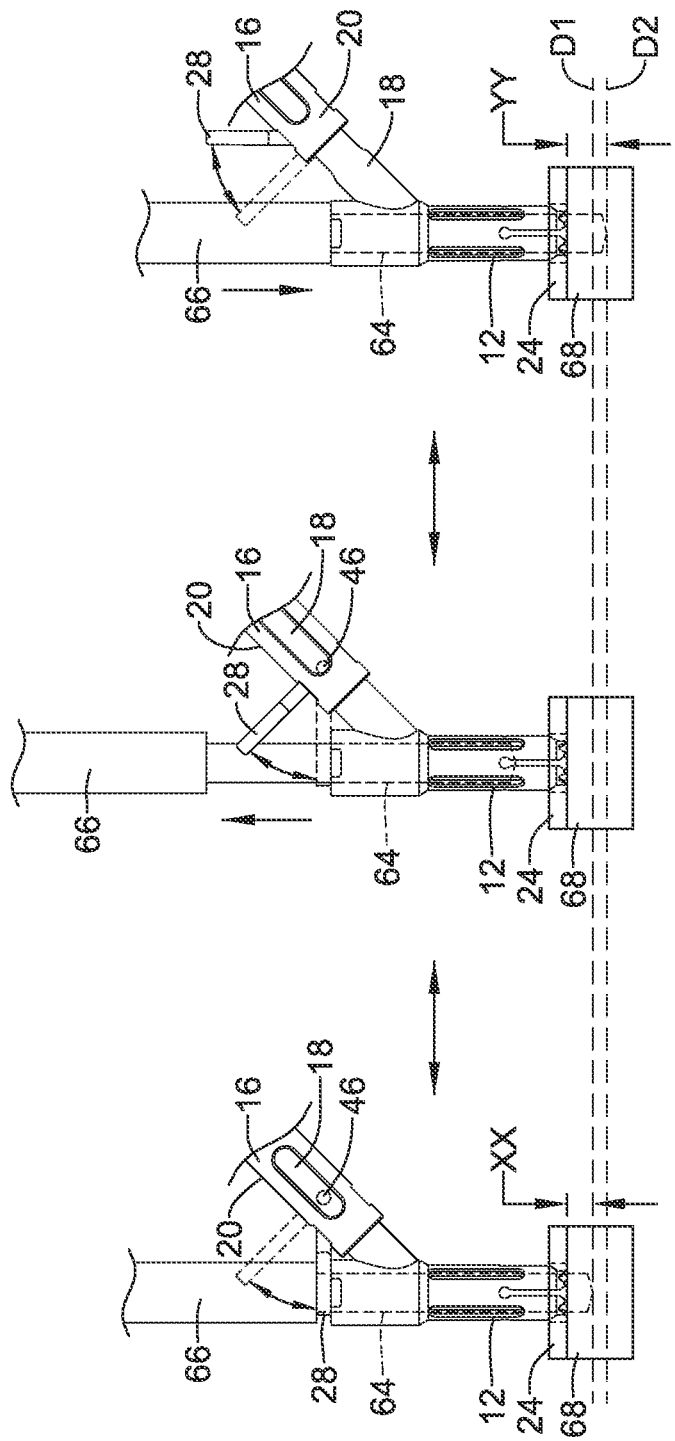
FIG. 10 is a schematic view of an illustrative method of adjusting a drill depth according to an aspect of the disclosure.

In some instances, as shown in FIG. 10, a drill bit 64 of a drill may be advanced through the through hole 32 of the spacer 28 and the lumen 34 of the guide member 12 such that a stop 66 of the drill bit 64 or drill may abut a proximal side of the spacer 28 when the drill bit 64 is advanced to a maximum extent XX from the distal end 12b of the guide member 12 corresponding to a first maximum depth $D_1$ in a patient's bone 68. When a user decides the drill bit 64 needs to be inserted into a bone 68 of a patient a further distance or to a deeper depth, the user may back the stop 66 drill away from the spacer 28 (i.e., withdraw the drill bit 64 proximally) while maintaining the drill bit 64 in the lumen 34 of the guide member 12 and/or the through hole 32 of the spacer 28. Once the drill bit 64 has been withdrawn proximally and the stop 66 has been backed away from the spacer 28 a sufficient amount while retaining the drill bit 64 within the lumen 34 of the guide member 12, the spacer 28 may be actuated to the second position spaced from the first end 12a of the guide member 12.

As the spacer 28 is actuated from the first position to the second position, the drill bit 64 may pass out of the hole 32 of the spacer 28 through the transverse opening 38 defined between the first end 40 and second end 40 of the spacer 28 in a direction transverse to the longitudinal axis of the hole 32 while retaining a distal portion of the drill bit 64 in the lumen 34 of the guide member 12.

After positioning the spacer 28 in the second position, the drill bit 64 may be advanced distally through the lumen 34 of the guide member 12 until the stop 66 of the drill or drill bit abuts the first end 12a of the guide member 12 to position the drill bit 64 at a deeper depth in which the drill bit 64 is advanced to a second maximum extent YY from the distal end 12b of the guide member 12 corresponding to a second maximum depth $D_2$ in the patient's bone 68.

In other instances, the guide device 10 may be used in a similar manner to prepare a pedicle or other bony structure to receive a bone screw, such as a pedicle screw, with or without a bone plate. For example, the distal end 12b of the guide member 12 may be positioned against the bony structure (e.g., a pedicle, vertebral body, facet, etc.). The guide device 10 may then be used to guide a drill bit, a tap, or other instrument through the lumen 34 of the guide member 12 during the installation procedure.

In some instances, a medical instrument, such as a drill bit, a tap, a probe or other medical instrument, may be advanced through the through hole 32 of the spacer 28 and the lumen 34 of the guide member 12 such that a stop of the medical instrument may abut a proximal side of the spacer 28 when the medical instrument is advanced to a maximum extent from the distal end 12b of the guide member 12 corresponding to a first maximum depth in a patient's bone. When a user decides the medical instrument needs to be inserted into a bone of a patient a further distance or to a deeper depth, the user may back the stop of the medical instrument away from the spacer 28 (i.e., withdraw the medical instrument proximally) while maintaining the medical instrument in the lumen 34 of the guide member 12 and/or the through hole 32 of the spacer 28. Once the medical instrument has been withdrawn proximally and the stop has been backed away from the spacer 28 a sufficient amount while retaining the medical instrument within the lumen 34 of the guide member 12, the spacer 28 may be actuated to the second position spaced from the first end 12a of the guide member 12.

As the spacer 28 is actuated from the first position to the second position, the medical instrument may pass out of the hole 32 of the spacer 28 through the transverse opening 38 defined between the first end 40 and second end 40 of the spacer 28 in a direction transverse to the longitudinal axis of the hole 32 while retaining a distal portion of the medical instrument in the lumen 34 of the guide member 12.

After positioning the spacer 28 in the second position, the medical instrument may be advanced distally through the lumen 34 of the guide member 12 until the stop of the medical instrument abuts the first end 12a of the guide member 12 to position the medical instrument at a deeper depth in which the medical instrument is advanced to a second maximum extent from the distal end 12b of the guide member 12 corresponding to a second maximum depth in the patient's bone.

Although certain steps of the method of operation may be discussed herein in one or more particular orders, it is contemplated one or more methods of operation may follow these steps in other orders (including a plurality of steps being performed simultaneously), may include one or more steps, or may include further steps in any order.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. An apparatus for guiding medical instruments used in attaching a bone plate, the apparatus comprising:
   a handle assembly including an inner shaft and an outer sleeve concentric about the inner shaft;

a guide member extending from the handle assembly, wherein the guide member has a first end, a second end, and a lumen therethrough from the first end to the second end;

a spacer coupled to the inner shaft and adjustably positionable at the first end of the guide member, the spacer being actuatable between a first position and a second position; and an actuation member operably coupled to the outer sleeve, wherein actuation of the actuation member causes longitudinal movement of the outer sleeve relative to the inner sleeve, thereby allowing adjustment of the spacer between the first position and the second position.

2. The apparatus of claim 1, wherein:
longitudinal movement of the outer sleeve in a first direction adjusts the spacer toward the first position adjacent the first end of the guide member; and
longitudinal movement of the outer sleeve in a second direction adjusts the spacer toward the second position spaced from the first end of the guide member.

3. The apparatus of claim 1, wherein the spacer is pivotably connected to the inner shaft of the handle assembly.

4. The apparatus of claim 3, wherein the spacer extends through an opening in the outer sleeve of the handle assembly.

5. The apparatus of claim 1, wherein the spacer has a through hole extending therethrough for receiving a drill bit.

6. The apparatus of claim 5, wherein:
the through hole is in axial alignment with a central longitudinal axis of the lumen extending through the guide member when the spacer is in the first position.

7. The apparatus of claim 5, wherein the through hole extending through the spacer is at least partially defined by a perimeter portion of the spacer having a first end and a second end separated from the first end, thereby allowing a drill bit to pass out of the through hole of the spacer in a transverse direction when the spacer is actuated to the second position while the drill bit is maintained in the lumen of the guide member.

8. The apparatus of claim 1, further comprising:
a locking mechanism configured to lock the actuation member in at least one of the first position and the second position.

9. The apparatus of claim 8, wherein the locking mechanism is a ball detent locking mechanism, the ball detent locking mechanism including a spherical member biased by a biasing member towards the inner shaft, the inner shaft including at least one detent for receiving the spherical member.

10. The apparatus of claim 8, wherein:
the inner shaft includes a first indentation and a second indentation; and
the locking mechanism engages the first indentation when the actuation member is in a first position corresponding to the first position of the spacer and the locking mechanism engages the second indentation when the actuation member is in a second position corresponding to the second position of the spacer.

11. An apparatus for guiding medical instruments used in attaching an occipital bone plate, the apparatus comprising:
a handle assembly including an actuation member, a first elongate member, and a second elongate member, the actuation member operatively coupled with the first elongate member and configured to control movement of the first elongate member relative to the second elongate member;

a guide member extending from the handle assembly, wherein the guide member has a first end, a second end, and a lumen extending therethrough from the first end to the second end;

a spacer operatively coupled with the second elongate member of the handle assembly and adjustably positionable at the first end of the guide member, wherein the spacer is pivotable between a first position and a second position; and a locking mechanism configured to lock the spacer in either the first position or the second position;

wherein actuation of the actuation member actuates the spacer between the first position and the second position.

12. The apparatus of claim 11, wherein the spacer includes a through hole at least partially defined by a perimeter portion of the spacer having a first end and a second end spaced apart from the first end, the spaced apart first and second ends configured to allow a drill bit to pass out of the through hole of the spacer in a transverse direction when the spacer is actuated to the second position while the drill bit is maintained in the lumen of the guide member.

13. The apparatus of claim 11, wherein the first elongate member comprises an outer sleeve and the second elongate member comprises an inner shaft positioned through the outer sleeve, the outer sleeve being longitudinally actuatable relative to the inner shaft.

14. The apparatus of claim 13, wherein:
the inner shaft includes a first indentation and a second indentation;
the locking mechanism engages the first indentation to lock the spacer in the first position; and
the locking mechanism engages the second indentation to lock the spacer in the second position.

15. A method of adjusting a drill depth, the method comprising:
positioning a guide member with a handle assembly extending therefrom adjacent a bone, wherein the guide member has a lumen extending therethrough from a first end of the guide member to second end of the guide member;
positioning a spacer operatively coupled to the guide member in a first position adjacent the first end of the guide member, the spacer including a hole therethrough in alignment with the lumen through the guide member; and
actuating the spacer to a second position while the spacer remains operatively coupled to the guide member, wherein the opening of the spacer is not aligned with the lumen through the guide member in the second position.

16. The method of claim 15, further comprising:
inserting a drill bit in a distal direction through the hole of the spacer and the lumen of the guide member with the spacer in the first position such that the drill bit extends a first distance from the distal end of the guide member;
withdrawing the drill bit proximally while maintaining the drill bit in the lumen of the guide member;
actuating the spacer to the second position while maintaining the drill bit in the lumen of the guide member; and
inserting the drill bit in a distal direction through the lumen of the guide member with the spacer in the second position such that the drill bit extends a second distance from the distal end of the guide member greater than the first distance.

17. The method of claim 15, wherein the spacer is pivotable between the first position and the second position.

* * * * *